(12) United States Patent
Siepmann et al.

(10) Patent No.: US 10,039,999 B2
(45) Date of Patent: Aug. 7, 2018

(54) ZEOLITES FOR SEPARATION OF ETHANOL AND WATER

(71) Applicants: Joern Ilja Siepmann, Hastings, MN (US); Peng Bai, Minneapolis, MN (US); Michael Tsapatsis, Minneapolis, MN (US)

(72) Inventors: Joern Ilja Siepmann, Hastings, MN (US); Peng Bai, Minneapolis, MN (US); Michael Tsapatsis, Minneapolis, MN (US)

( * ) Notice: Subject to any disclaimer, the term of this patent is extended or adjusted under 35 U.S.C. 154(b) by 0 days.

(21) Appl. No.: 15/327,722

(22) PCT Filed: Jul. 22, 2015

(86) PCT No.: PCT/US2015/041566
§ 371 (c)(1),
(2) Date: Jan. 20, 2017

(87) PCT Pub. No.: WO2016/014682
PCT Pub. Date: Jan. 28, 2016

(65) Prior Publication Data
US 2017/0203233 A1    Jul. 20, 2017

Related U.S. Application Data

(60) Provisional application No. 62/027,529, filed on Jul. 22, 2014.

(51) Int. Cl.
| | |
|---|---|
| *C07C 29/76* | (2006.01) |
| *B01D 15/08* | (2006.01) |
| *C12P 7/06* | (2006.01) |
| *B01J 20/18* | (2006.01) |
| *B01J 20/28* | (2006.01) |

(52) U.S. Cl.
CPC .......... *B01D 15/08* (2013.01); *B01J 20/18* (2013.01); *B01J 20/28033* (2013.01); *C07C 29/76* (2013.01); *C12P 7/06* (2013.01)

(58) Field of Classification Search
CPC .. C07C 29/76; C12P 7/06; B01D 15/08; B01J 20/18
USPC ........................................................ 568/917
See application file for complete search history.

(56) References Cited

U.S. PATENT DOCUMENTS

| | | | | |
|---|---|---|---|---|
| 5,554,286 A | * | 9/1996 | Okamoto | B01D 61/362 210/500.25 |
| 5,755,967 A | * | 5/1998 | Meagher | B01D 61/362 210/640 |
| 6,287,645 B1 | | 9/2001 | Balkus, Jr. et al. | |
| 2008/0214686 A1 | | 9/2008 | Suzuki et al. | |
| 2008/0217247 A1 | * | 9/2008 | Niino | B01D 61/362 210/651 |
| 2009/0120875 A1 | | 5/2009 | Liu et al. | |
| 2010/0018926 A1 | | 1/2010 | Liu et al. | |
| 2012/0000358 A1 | | 1/2012 | Kawai et al. | |
| 2012/0240763 A1 | | 9/2012 | Liu et al. | |

FOREIGN PATENT DOCUMENTS

| | | |
|---|---|---|
| WO | WO-2014056965 A1 | 4/2014 |
| WO | WO-2016014682 A1 | 1/2016 |

OTHER PUBLICATIONS

"International Application Serial No. PCT/US2015/041566, International Search Report dated Oct. 23, 2015", 4 pgs.
"International Application Serial No. PCT/US2015/041566, Written Opinion dated Oct. 23, 2015", 8 pgs.
"International Application Serial No. PCT/US2015/041566, International Preliminary Report on Patentability dated Feb. 2, 2017", 10 pgs.

* cited by examiner

*Primary Examiner* — Sikarl A Witherspoon
(74) *Attorney, Agent, or Firm* — Schwegman Lundberg & Woessner, P.A.

(57) ABSTRACT

A process for separating ethanol from a mixture including ethanol and water comprises contacting the mixture with a sorbent or membrane including one or more zeolites having a high adsorption selectivity toward ethanol over water, wherein at least a fraction of the ethanol from the mixture is adsorbed by the sorbent or membrane and an unadsorbed portion of the mixture forms a raffinate having a lower concentration of ethanol than the mixture. The process further includes releasing adsorbed ethanol from the sorbent or membrane as a retentate or a permeant to produce an ethanol extract having a higher concentration of ethanol than the mixture.

21 Claims, 4 Drawing Sheets

ZEOLITES FOR SEPARATION OF ETHANOL AND WATER

CROSS-REFERENCE TO RELATED APPLICATION

This application is a U.S. national stage application filed under 35 U.S.C. § 371 from International Application No. PCT/US2015/041566, filed Jul. 22, 2015, entitled "ZEOLITES FOR SEPARATION OF ETHANOL AND WATER," which claims priority to U.S. Provisional Application Ser. No. 62/027,529, filed on Jul. 22, 2014, the disclosures of which are expressly incorporated herein by reference as if reproduced in their entirety.

GOVERNMENT FUNDING

This invention was made with government support under DE-FG02-12ER16362 awarded by Department of Energy. The government has certain rights in the invention.

TECHNICAL FIELD

This disclosure relates to a class of processes for separating and concentrating ethanol from a feed mixture containing said component and water using highly selective zeolite materials.

BACKGROUND

Fossil fuels are non-renewable resources, and there have been continued efforts towards developing sustainable alternatives such as biofuels. Bioethanol, for example, can be used as motor fuels alone or as a high-octane-number and CO-reducing additive to gasoline. However, a significant challenge exists for the production of fuel ethanol via biomass conversion, which is related to the separation of the desired ethanol from its relatively dilute aqueous solution. This separation is traditionally carried out by distillation, which consumes a large amount of energy. Although the heat input required for distillation can come from sources other than the product fuel (e.g., burning feed residues) in certain cases (e.g., sugarcane-based technology), it is not possible for all ethanol production technologies nor desirable if the feed residues can find other uses (e.g., in a lignocellulosic ethanol plant). In addition, if anhydrous ethanol with concentrations exceeding the ethanol-water azeotrope concentration is required, then a more energy-intensive azeotropic distillation step is conventionally needed.

Zeolites play numerous important roles in modern petroleum refineries and have the potential to advance the production of fuels and chemical feedstocks from renewable resources. The performance of a zeolite as separation medium can depend on its framework structure and the type or location of active sites. To date, 213 framework types have been synthesized and >330,000 thermodynamically accessible zeolite structures have been predicted. Hence, identification of optimal zeolites for a given application from the large number of candidate structures is attractive for accelerating the pace of materials discovery.

Separating ethanol from its aqueous solution, a process essential for biofuel production, has traditionally relied on energy-intensive distillation. Nearly defect-free silicalite-1, an all-silica zeolite with the framework type MFI, has been proposed as an effective sorbent and membrane for this separation.

Certain porous materials can be used to separate a component from a mixture by selective adsorption or transport. For example, $K^+$-exchanged aluminosilicates of the LTA type (Zeolite 3A) strongly adsorb water while not allowing ethanol to pass through. Processes utilizing LTA-type zeolites to further dry ethanol after the primary distillation, for example to replace azeotropic distillation, are disclosed in U.S. Pat. Nos. 2,137,605, 4,273,621, 4,407,662, 4,465,875, and 2010/0081851.

Adsorptive separation processes aimed to replace primary distillation have also been reported. U.S. Pat. No. 4,277,635 discloses a liquid phase adsorption technique using MFI-type silicalite as the sorbent to extract ethanol. The residual stream can be displaced by highly concentrated ethanol under laminar flow condition, which according to U.S. Pat. No. 4,277,635 results in substantially no intermixing and the product is of gasohol quality. U.S. Pat. No. 4,343,623 further improves the hydrophobicity of the silicalite sorbent via esterification of surface hydrophilic sites. U.S. Pat. No. 4,382,001 discloses the use of a hydrophobic activated carbon as the sorbent and a compound such as isooctane as the desorbent so that the product can be directly blended into gasoline. Canadian 1195258 discloses a separation process also using silicalite as sorbent, but based on vapor phase adsorption. Carrying out adsorption in the vapor phase for a stripping gas sufficiently rich in ethanol improves ethanol recovery and avoids the possibility of solids contained in the dilute solution plugging the porous sorbent. U.S. Pat. Nos. 4,061,724 and 4,073,865 describe the synthesis of silicalite and F-silicalite.

SUMMARY

This disclosure describes a set of zeolite framework types (identified each by a three-letter code as defined by the Structure Commission of the International Zeolite Association) that have high selectivity and capacity for ethanol but whose use in the separation of ethanol/water mixtures have not been disclosed or suggested before. These zeolites can be used in a variety of processes for separating and concentrating ethanol from a feed mixture containing the ethanol and water.

In an example, a class of processes comprises contacting a feed mixture comprising ethanol and water with one or more zeolites, the framework types of which are selected based on two metrics, the selectivity over water and the ethanol capacity, with either an equilibrium adsorption or a continuous permeation set-up, in one or more separation units. The residual feed (raffinate) either remains in or is recycled back to the feed source. The adsorbed phase can be desorbed to yield anhydrous ethanol of high purity.

and high w=15% (bottom row): (a) FER at w=0.43%, (b) MFI at 0.43%, (c) VFI* at 0.12%, (d) FER, (e) MFI, and (f) ATN*. Silicon, oxygen, carbon, and hydrogen atoms are shown as yellow, cyan, and white, respectively. Isosurfaces equidistant to framework atoms are shown in gray.

Figure 4:
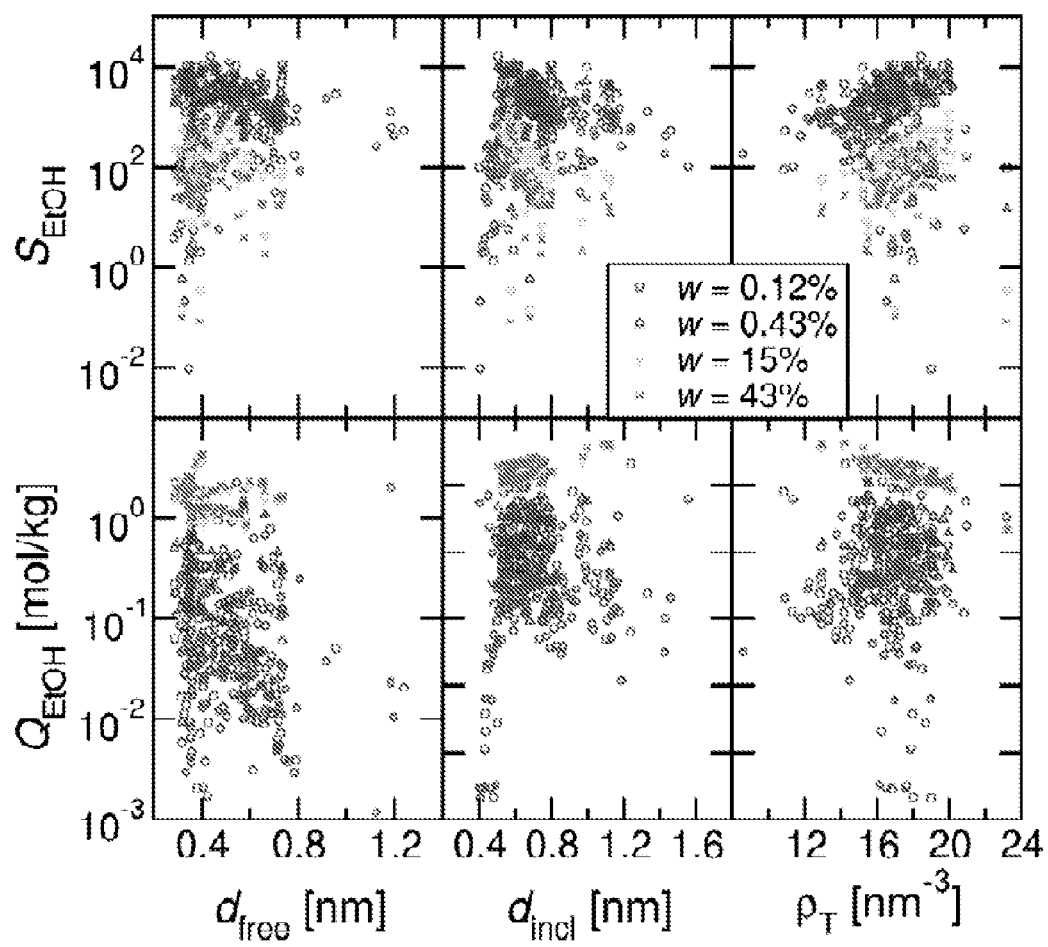

FIG. 4 illustrates $S_{EtOH}$ (top) and $Q_{EtOH}$ (bottom) as a function of the diameter of the largest free-roaming sphere ($d_{free}$, left), the diameter of the largest included sphere along the free sphere path ($d_{incl}$, middle), and the density of framework T atoms ($\rho_T$, right).

DETAILED DESCRIPTION

Sugar fermentation can produce ethanol in an ethanol concentration range between 5-15 wt %, depending on the sugar and yeast combination, after which point fermentation is significantly inhibited. Typical fuel blends require anhydrous ethanol with a water content of less than 1 wt % (ASTM D4806, D4814, and D5798). For blending into hE15 (15% hydrous ethanol and 85% gasoline) used in vehicles in the Netherlands and Brazil, the ethanol blend can contain up to 4.4 wt % water.

The present disclosure describes a class of energy-efficient processes, based on the use of zeolite sorbents that are highly selective towards ethanol over water. The zeolite sorbents can separate ethanol from the fermentation product to the substantial exclusion of water. Thereafter, anhydrous ethanol of high purity can be recovered. The inventors have identified, through a large-scale, multi-step computational screening process, promising zeolite structures having the ability to exceed the ethanol-water azeotropic concentration in a single separation step from fermentation broths.

The processes can comprise contacting a mixture including ethanol and water (also referred to herein as a "feed mixture") with one or more selected zeolite sorbents. The terms "feed mixture," "ethanol and water mixture," "ethanol-water mixture," or simply "mixture," as used herein, can comprise one or both of a liquid-based mixture that includes ethanol and water and a vapor-based mixture that includes ethanol and water. A liquid-based ethanol-water mixture can include one or more liquid components other than ethanol and water, one or more solid components carried by the liquid, or one or more entrained vapor components that may be ethanol or water or another compound. For example, the ethanol-water mixture can comprise a fermentation broth resulting from the fermentation of a fermentable feedstock, such as: one or more sugars; one or more starches; one or more grains; or other plant matter, such as one or more fruits, one or more vegetables, one or more cellulosics (e.g., wood, one or more grasses, or other plant matter comprising at least one of cellulose, hemicellulose, and lignocellulose), or parts thereof. A vapor-based ethanol-water mixture can include compounds other than ethanol or water, such as air or other compounds. For example, a vapor-based ethanol-water mixture can include a vapor generated by heating or vacuuming a fermentation broth, a stripping gas enriched in ethanol and water, or an ethanol-water mixture produced in any other way and combinations thereof.

The one or more zeolites that the ethanol-water mixture is contacted with can comprise one or more zeolite materials that have a high adsorption selectivity toward ethanol over water. The one or more zeolites can take any form that will put the feed mixture in sufficient contact with the one or more zeolite materials and allow for adsorption of at least a fraction of the ethanol in the ethanol-water mixture. Examples of physical structures that the one or more zeolites can take include, but are not limited to, a zeolite sorbent or a membrane comprising the one or more zeolite materials.

The feed mixture can be contacted with the zeolite sorbents in one or more separation units. Contact between the feed mixture and the zeolite sorbents can be performed, under equilibrium conditions, near equilibrium conditions, or continuous operation conditions. The raffinate from the contacting operation can be recycled back to the feed source or used in some other way. The adsorbed phase (e.g., enriched in ethanol) can be desorbed from the zeolite sorbent, such as by reducing the external pressure, increasing the temperature, passing a non-adsorbing gas at either normal or elevated temperatures through the sorbent, or combinations thereof. Depending on the final concentration of the raffinate in the adsorption step, the adsorbed phase can either be already highly concentrated, e.g., with at least about 95.6 wt % ethanol, or can be moderately concentrated, in which case the desorbed mixture can be connected to a second set of separation units, where a similar procedure with different zeolite sorbents can be used to further separate and concentrate ethanol to the desired purity.

All-silica zeolites by themselves can be very hydrophobic, but the adsorption of ethanol can promote water co-adsorption through hydrogen-bond formation and lower selectivity. For this application, the desired zeolite possesses a pore/channel system that accommodates ethanol molecules but disfavors hydrogen bonding with water molecules.

As described above, zeolites have been proposed for adsorption of ethanol from mixtures containing water and ethanol. However, the zeolites currently described in the art are not selective or efficient enough for this purpose. Moreover, experimental testing of all existing known zeolites for a given application would be very time and labor intensive, sometimes even infeasible when a synthesis protocol for the material with the desired composition is not yet developed. In addition, the possible number of synthesizable zeolites is enormously large, with some of the structures found in the predicted crystallography open database (PCOD) possessing potentially much better characteristics. Selecting optimal candidate materials through predictive modeling is hence a very attractive proposition. Such screening studies have so far focused mostly on single-component adsorption of small, rigid, non-hydrogen-bonding molecules, such as $H_2$, $CH_4$, and $CO_2$. Screening sorbents and catalysts for complex mixtures composed of large, articulated molecules, where advanced algorithms are required for sampling the distribution of thousands of conformers, or polar, hydrogen-bonding molecules, where an accurate description of electrostatics and the resulting mixture non-idealities are of paramount importance, has so far been an intractable problem. Enabled by a multistep screening workflow, efficient sampling algorithms, accurate force fields, and a two-level parallel execution hierarchy utilizing up to 131,072 computer cores on a supercomputer at Argonne National Laboratory, the inventors have engaged in high-throughput-screening for separation of ethanol from water.

The sorbent zeolite can comprise a channel system. The term "channel system," as used herein, can refer to a crystalline zeolite with pores which can have a circular or elliptical cross section, or generally circular or elliptical, that is formed by the framework atoms of the zeolite. The pore dimension of the channel system can be measured as the diameter of the largest circle that fits into the cross section, e.g., with a circumference at least 0.28 nm away from any framework oxygen atom making up the pore. In an example, the pore diameter can be less than 0.6 nm. The sorbent zeolite can also comprise a cage system, which can be in place of or in addition to the channel system. The term "cage system," as used herein, can refer to a crystalline zeolite where spherical or ellipsoidal void spaces, called cages, make up the predominant fraction of the accessible pore volume that is formed by the framework atoms. The cages can be separated by narrower windows with general circular or elliptical cross section that can provide connection between the cages. The cage dimension can be measured as the diameter of the largest sphere that fits into the void space, e.g., with a surface at least 0.28 nm away from any framework oxygen atom making up the pore. The window dimension is measured as the diameter of the largest circle that fits into the cross section, i.e., with a circumference at least 0.28 nm away from any framework oxygen atom making up the pore. In an example, the diameter of the cage is less than 1.2 nm, for example less than 1 nm, and the window connecting the nearest cages is less than 0.5 nm, for example less than 0.4 nm. In an example, the feed mixture can be brought into contact with a zeolite sorbent, e.g., in one or more adsorption units. The zeolite sorbent has a high selectivity and a sufficient capacity for ethanol over the 5-15 wt % ethanol concentration in the feed mixture. Examples of such zeolites are the ATN or FER types, allowing the raffinate to reach a concentration not less than 1-5 wt % ethanol. For example, a feed mixture containing about 15 wt % ethanol can be reduced to about 12 wt % after being passed through the sorbent zeolites. The raffinate can remain or can be recycled back to the fermentation source. The loaded zeolite sorbents can be separated from the raffinate and desorbed to yield highly-concentrated ethanol of at least 95.6 wt %.

In an example process, the feed mixture can be brought into contact in a single adsorption unit with a zeolite sorbent having a high capacity and a reasonable selectivity for ethanol, such as a VFI-type zeolite. The contacting between the feed mixture and the zeolite sorbent can be at equilibrium or near equilibrium. The raffinate can reach a concentration below 1-3 wt % and the adsorbed phase can contain more than 20 wt % ethanol, such as more than 42 wt % ethanol. The raffinate can be displaced and recycled. The adsorbed ethanol can be desorbed and brought into contact in a second adsorption unit with a second zeolite sorbent having a high selectivity and a sufficient capacity for ethanol at the corresponding concentration, such as zeolites of the ATN or FER types. The end product can be a highly-concentrated ethanol of at least 95.6 wt %.

In an example process, the feed mixture can be continuously contacted with a zeolite membrane having a high selectivity for ethanol, such as membranes made from zeolites of the ATN or FER types. On the other side of the membrane, ethanol can be continuously or semi-continuously extracted at high purity of at least 95.6 wt %.

Example

The present disclosure can be further understood by reference to the following example which is offered by way of illustration. The present disclosure is not limited to the example given herein.

Figure 1:
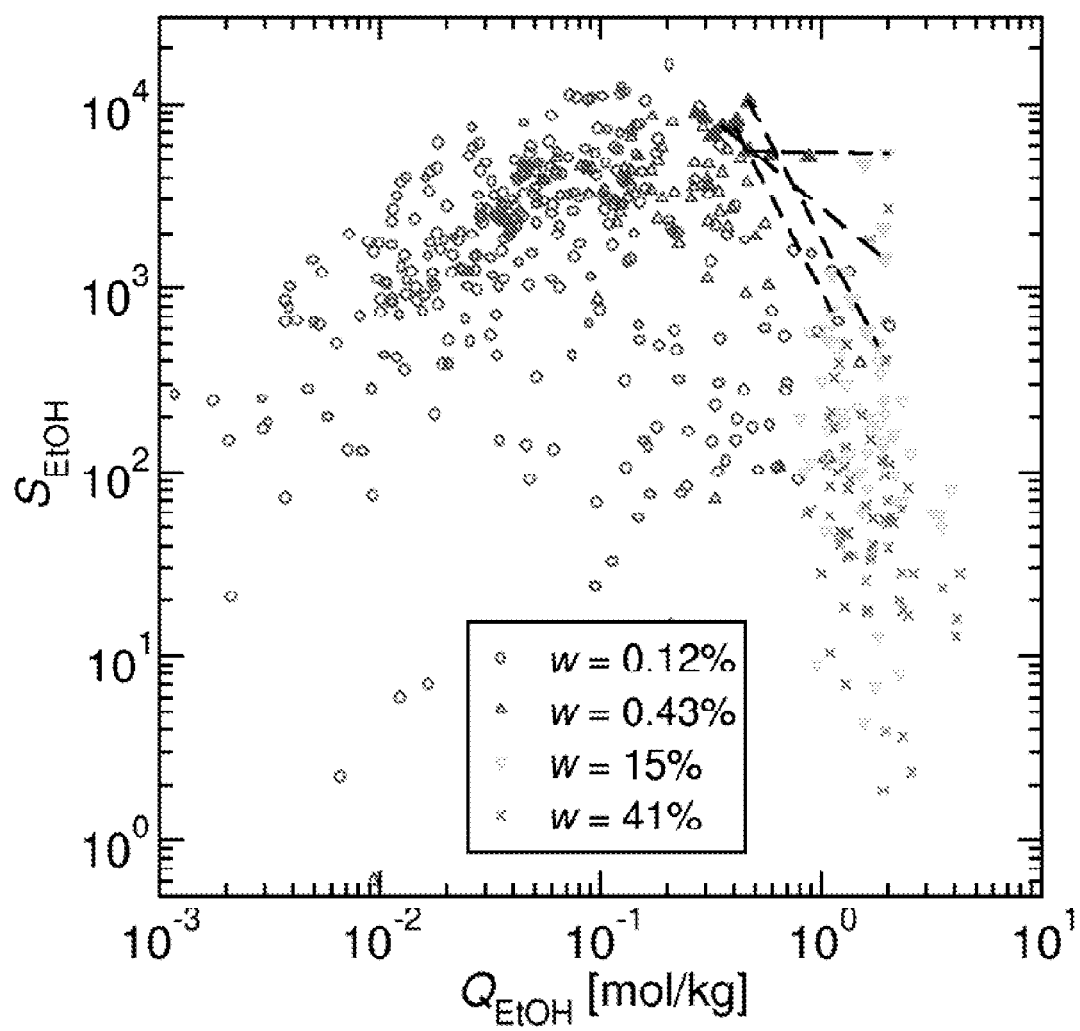
FIG. 1 illustrates the relationship of $S_{EtOH}$ versus $Q_{EtOH}$ at different solution concentrations (w). Filled symbols highlight the 10 highest ranked structures at w=0.43 and 15% and dashed lines connect those structures found among the top-10 for both w.

Sugar fermentation produces ethanol with solution-phase concentrations from w=5 to 15 wt % at temperatures from 298 to 323 K depending on the yeast/sugar combination. A separation process with a zeolite sorbent should extract ethanol from the fermentation broth to as high a degree as possible, and the final w in equilibrium with the adsorbed phase may be very low. Based on these process targets, Monte Carlo simulations at w=0.12 wt % and T=323 K were carried out to screen all of the framework structures available from the Structure Commission of the International Zeolite Association, IZA-SC. The product of ethanol selectivity, $S_{EtOH}$ (=r(1−w)/(1−r)w was used, where r is the concentration of the retentate), and loading, $Q_{EtOH}$, to rank the zeolite structures. This performance metric, $P_{EtOH}$, is rather robust and effective in identifying the top structures at a given target w. Operating to such a low w, none of the candidate structures can achieve the selectivity target, $S_{target} \geq 18000$, that would be required for the retained phase to exceed the ethanol/water azeotropic point (95.6 wt %) in a single extraction step, but some come close. Hence, the adsorption at three higher w values for the 64 structures with the highest $P_{EtOH}$ values and satisfying the additional constraint $Q_{EtOH} > Q_{water}$ emerging from this initial screening step were investigated. As illustrated in FIG. 1, $S_{EtOH}$ decreases at a slower rate than w increases for many zeolite structures. Thus, by raising w to 0.43 wt %, 18 structures capable of reaching a sufficiently high $S_{EtOH}$ to exceed the azeotropic point ($S_{target} \geq 5100$) were found. As a result, this w value is used to rank all zeolite structures.

Figure 2:
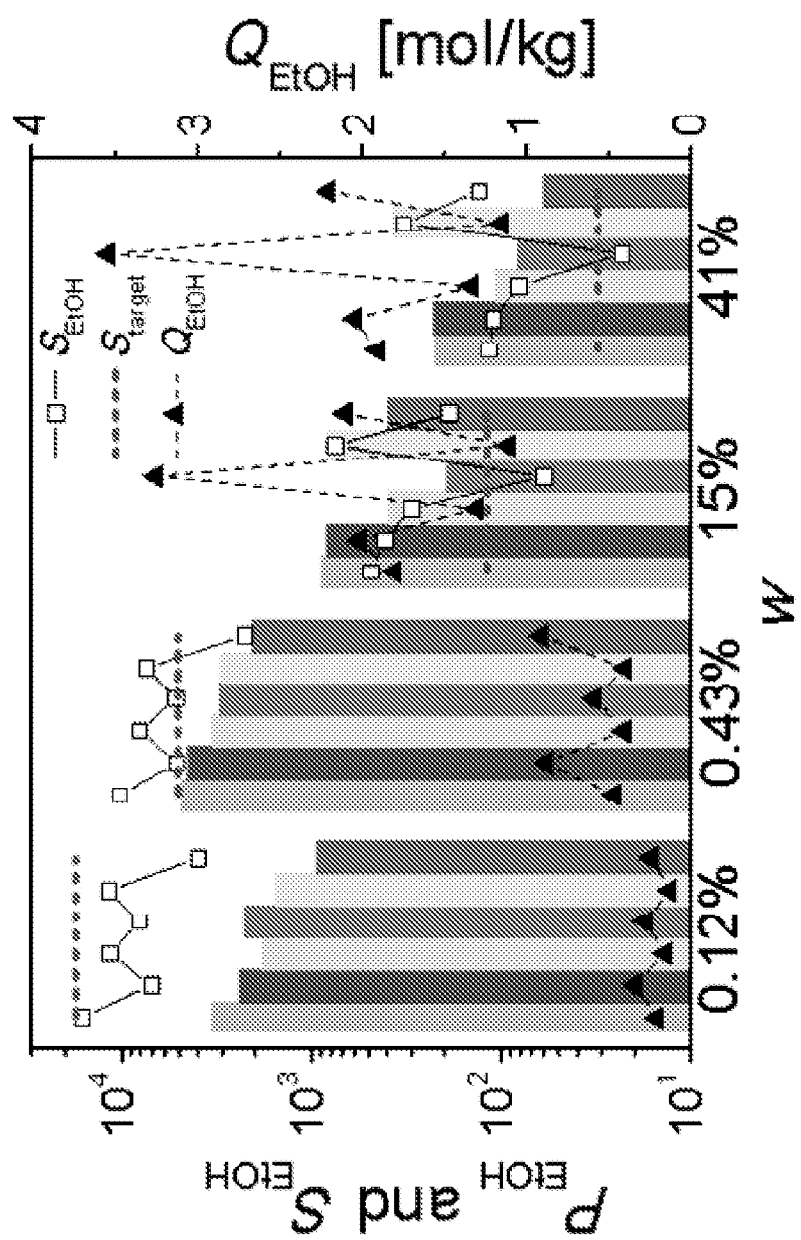
FIG. 2 illustrates the adsorption characteristics ($P_{EtOH}$, bars; $S_{EtOH}$, squares; $Q_{EtOH}$, triangles) for the top-5 zeolites at w=0.43%: FER (green), OWE* (blue), ESV* (cyan), UFI* (magenta), and MRE (yellow), with data for MFI (brown) shown for comparison. The horizontal red lines indicate $S_{target}$=0.956(1−w)/0.044w.

The adsorption characteristics of the top-5 framework types are compared to MFI in FIG. 2. Numerical data for the 10 best performing zeolites are provided in TABLE 1.

TABLE 1

Ethanol selectivity ($S_{EtOH}$) and loading ($Q_{EtOH}$ in mol/kg) at different solution concentrations (w). Data for MFI is provided for comparison. The target $S_{target}$ is the value required to exceed the azeotropic concentration.

| Zeolite | w = 0.12% | | w = 0.43% | | w = 15% | | w = 41% | |
|---|---|---|---|---|---|---|---|---|
| | S | Q | S | Q | S | Q | S | Q |
| FER | 16000 | 0.21 | 10000 | 0.47 | 490 | 1.8 | 120 | 1.9 |
| OWE* | 7000 | 0.34 | 5200 | 0.88 | 410 | 2.0 | 110 | 2.0 |
| ESV* | 12000 | 0.16 | 8100 | 0.41 | 300 | 1.3 | 81 | 1.3 |
| UFI* | 8100 | 0.28 | 5200 | 0.59 | 60 | 3.2 | 23 | 3.5 |
| MRE | 12000 | 0.13 | 7400 | 0.41 | 760 | 1.1 | 330 | 1.2 |
| ZON† | 8500 | 0.12 | 7500 | 0.36 | 1500 | 1.9 | 400 | 2.0 |
| ATN* | 5600 | 0.15 | 5600 | 0.47 | 5400 | 2.0 | 2700 | 2.0 |
| MAZ* | 13000 | 0.12 | 8300 | 0.30 | 79 | 1.6 | 33 | 1.7 |
| ZON* | 12000 | 0.10 | 7400 | 0.29 | 2100 | 1.9 | 660 | 2.0 |
| SAT* | 4400 | 0.19 | 2200 | 0.56 | 200 | 2.0 | 70 | 2.0 |
| MTT | 7900 | 0.06 | 5800 | 0.19 | 1200 | 1.3 | 490 | 1.3 |
| STI* | 4800 | 0.10 | 3500 | 0.30 | 250 | 2.0 | 56 | 2.1 |
| EAB* | 1600 | 0.22 | 1900 | 0.51 | 240 | 2.3 | 82 | 2.5 |
| CDO | 7900 | 0.05 | 6600 | 0.14 | 580 | 1.6 | 150 | 1.7 |
| CGF* | 6600 | 0.06 | 4800 | 0.18 | 4800 | 1.6 | 1800 | 1.7 |
| EZT* | 4000 | 0.05 | 3000 | 0.19 | 160 | 2.2 | 62 | 2.3 |
| AFO* | 5700 | 0.03 | 4400 | 0.09 | 500 | 1.1 | 99 | 1.2 |
| ATO* | 6700 | 0.03 | 4400 | 0.09 | 510 | 1.1 | 170 | 1.2 |
| AEL* | 4600 | 0.03 | 3200 | 0.10 | 420 | 1.2 | 110 | 1.3 |
| MFI | 4000 | 0.24 | 2300 | 0.91 | 190 | 2.1 | 60 | 2.2 |
| VFH*,‡ | 620 | 2.05 | — | — | — | — | — | — |
| $S_{target}$ | 18000 | | 5100 | | 120 | | 31 | |

*Idealized siliceous structure.
†Zinc-containing aluminophosphate.
‡Zeolite with $Q_{water} > Q_{EtOH}$ at w = 0.12%

FER is the top-ranked structure at w=0.12 and 0.43% due to its exceptionally high $S_{EtOH}$, and remains among the top-10 structures at w=15%. Its retentate exceeds the azeotropic composition for w≥0.43%. In contrast, MFI only exceeds $S_{target}$ for the two higher w, and is not among the top-10 structures at any w. Three of the other top-5 structures (OWE*, ESV*, UFI*) currently exist only as aluminosilicates or aluminophosphates, whose adsorption properties may be different from the idealized siliceous structures (indicated by * added to the three-letter code) used for the screening. Nonetheless, the siliceous forms of these framework types will be attractive synthesis targets.

As indicated in FIG. 1, one sees the typical compromise between selectivity and capacity: increasing w leads to increasing $Q_{EtOH}$ and decreasing $S_{EtOH}$ due to enhanced water coadsorption. Selectivities at w=0.43% are a poor indicator of those at w=15% (with a correlation coefficient of $R^2=0.31$), whereas $S_{EtOH}$ values at the two lower and the two higher concentrations are reasonably well correlated. This behavior can be attributed to the fact that, for most frameworks, $Q_{EtOH}$ at w=0.43% is less than ⅓ of the value at w=15% which in turn falls within 10% of $Q_{EtOH}$ at w=41%; i.e., near saturation loading is achieved at w=15%, the typical upper bound for fermentation broths. For these highly non-ideal mixtures, the screening process must consider multiple feed concentrations and cannot simply rely on data at one w. Data at multiple w also allows us to find suitable combinations for a two-step separation utilizing two different zeolites. For example, structure VFI* reaches $Q_{EtOH}$>2.0 mol/kg already at w=0.12%, but with a relatively modest $S_{EtOH}$=620. The retentate of this adsorption yields r=43% and can be used as feed for another adsorption with ATN* that offers the highest $S_{EtOH}$ at w≥15%. To optimize the operating conditions for each material or combination, the full adsorption isotherms and diffusivities will need to be computed.

Figure 3:
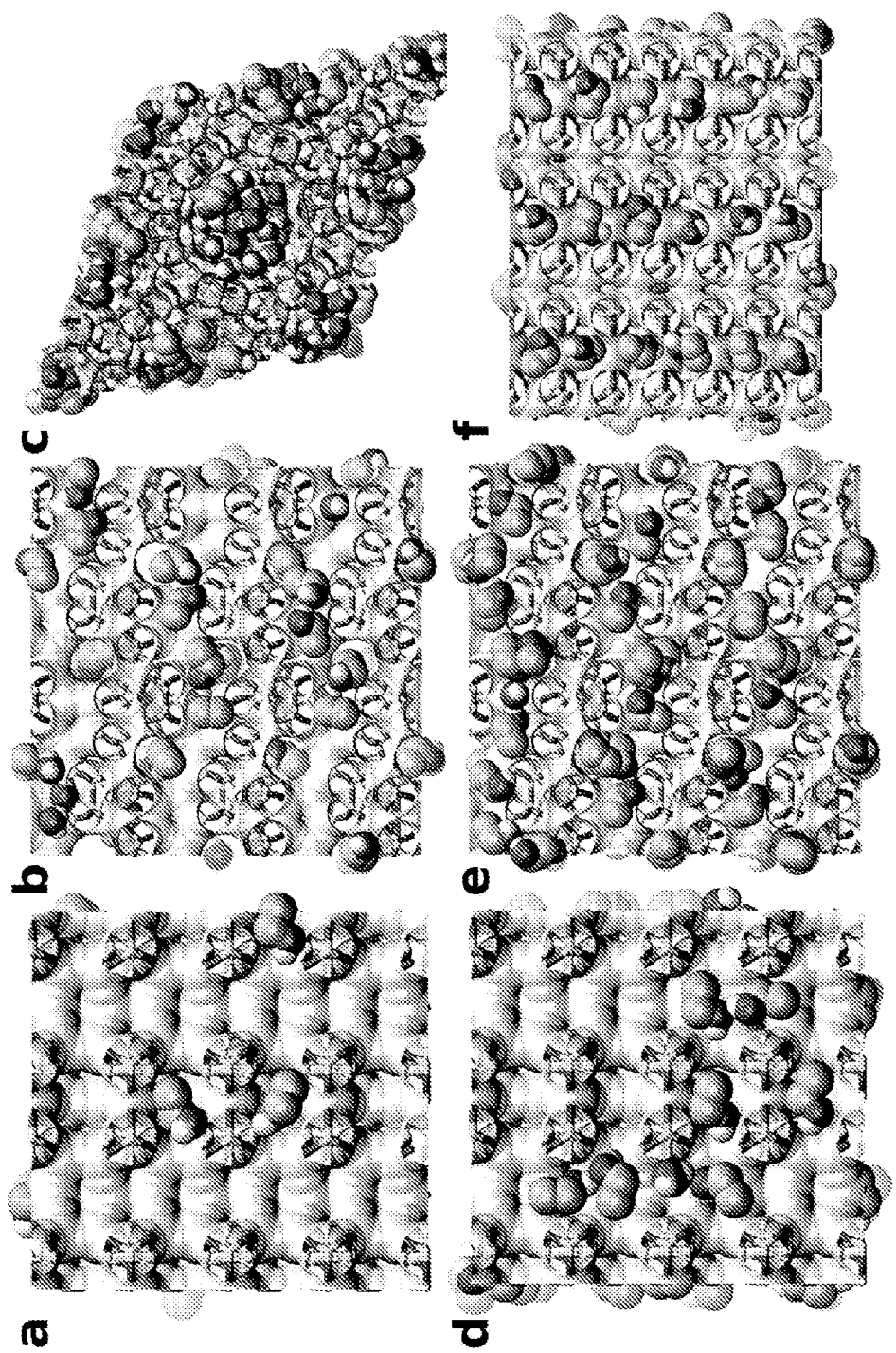
FIG. 3 shows the snapshots of representative sorbate configurations inside zeolite frameworks at low (top row)

Previous screening studies for simpler sorbates have focused on finding structure-property relationships with the goal of identifying the geometric motifs responsible for the high performance of certain materials. However, the ethanol/water mixture exhibits significant non-idealities in both the solution and adsorbed phases due to strong intermolecular interactions, and the common geometry—performance correlations do not appear to hold well (see FIG. 4). FIG. 3 contrasts the siting of the adsorbed molecules at w=0.43% in FER with that in MFI, a zeolite heavily explored in the literature for its potential to separate ethanol from its aqueous solution. In MFI, the enlarged intersection regions of the two channel systems facilitate water molecules with multiple hydrogen bonds, which reduces the energetic penalty for transferring water from its bulk environment and lowers the selectivity for ethanol. On the other hand, the distribution of adsorption sites in FER is such that two adjacent favorable sites for ethanol are spaced far enough apart that an extended hydrogen-bonding network involving water is not formed. At w=15%, ethanol populates the other FER channels that permit some hydrogen bonding and $S_{EtOH}$ decreases 2-fold. As seen in FIG. 3, the high $Q_{EtOH}$ and modest $S_{EtOH}$ in VFI* are due to 1.2 nm channels that are less hydrophobic than smaller channels and allow for significant loading ($Q_{water}$>$Q_{EtOH}$) even at w=0.12%, whereas the high $S_{EtOH}$ in ATN* at high w=15% is caused by well-spaced ethanol adsorption sites separated by narrow windows.

Methods

Framework Structures.

The IZA-SC database used in the screening comprises a set of idealized framework structures and other experimentally determined structures. The database is provided by Baerlocher & McCusker at www.iza-structure.org/databases as "Database of zeolite structures," the entire content of which is incorporated by reference as if reproduced herein in its entirety. The idealized structure for each framework type is obtained by geometric refinement with prescribed interatomic distances, assuming a (hypothetical) $SiO_2$ composition, and in the highest possible symmetry space group of the framework type. The experimental structures are included if they contain only O, Si, Al, P, or H atoms. Solvent molecules and ions were removed, and partial occupation were randomly assigned at the unit cell level.

Simulation Methods.

The transferable potentials for phase equilibria (TraPPE) force field is utilized to describe the sorbate-sorbate and sorbate-zeolite interactions modelled via Lennard-Jones (LJ) and Coulomb potentials. In our simulations, the zeolite frameworks are assumed to be rigid, while sorbate molecules sample angle bending and dihedral motions. To improve computational efficiency, grid files for the interaction energy of a test particle with the zeolite were generated in a manner that contains the repulsive LJ, attractive LJ, and the short- and long-range Coulomb components, but is independent of the specific force field parameters for the sorbate molecule; therefore the same grid files can facilitate screening calculations for other applications. Configurational-bias Monte Carlo simulations in the grand-canonical ensemble (CB-GCMC) were used to compute the sorbate loadings as function of the ethanol/water bulk solution concentration using chemical potentials obtained from previous Gibbs ensemble simulations with explicit solution phases. In the infinite-dilution limit, these CB-GCMC simulations also yield directly $k_H$ and $\Delta H_{ads}$. To carry out the energy grid tabulation and CB-GCMC simulations in a high-throughput fashion, a two-level parallel execution hierarchy exploring simultaneously $2^7$ to $2^{14}$ zeolite structures and accelerating the simulations for each structure by spreading the computational load over $2^2$ to $2^8$ computer cores was implemented. These massively-parallel screening calculations can be performed on a supercomputer.

Exemplary Embodiments

To better illustrate the processes and zeolite materials of the present disclosure, a non-limiting list of EMBODIMENTS is provided here:

EMBODIMENT 1 can include subject matter (such as an apparatus, a device, a method, or one or more means for performing acts), such as can include a process for separating ethanol from a mixture including ethanol and water. The subject matter can include contacting the mixture with a sorbent or membrane including one or more zeolites having a high affinity to ethanol over water, wherein at least a fraction of the ethanol from the mixture is adsorbed by the sorbent or membrane and an unadsorbed portion of the mixture forms a raffinate having a lower concentration of ethanol than the mixture, and releasing adsorbed ethanol from the sorbent or membrane as a retentate or a permeant to produce an ethanol extract having a higher concentration of ethanol than the mixture.

EMBODIMENT 2 can include subject matter (such as an apparatus, a device, a method, or one or more means for performing acts), such as can include a process for separating ethanol from a mixture including ethanol and water. The subject matter can include contacting the mixture with a sorbent or membrane including one or more zeolites selected from the group consisting of an FER-type zeolite, an MRE-type zeolite, an MU-type zeolite, an ATN-type zeolite, a ZON-type zeolite, an OWE-type zeolite, an ESV-type zeolite, a CGF-type zeolite, an MAZ-type zeolite, a CDO-type zeolite, an STI-type zeolite, an AFO-type zeolite, an AEL-type zeolite, an ATO-type zeolite, and an EZT-type zeolite, wherein at least a fraction of the ethanol from the mixture is adsorbed by the sorbent or membrane and an unadsorbed portion of the mixture forms a raffinate having a lower concentration of ethanol than the mixture, and releasing adsorbed ethanol from the sorbent or membrane as a retentate or a permeant to produce an ethanol extract having a higher concentration of ethanol than the mixture.

EMBODIMENT 3 can include subject matter (such as an apparatus, a device, a method, or one or more means for performing acts), such as can include a process for separating ethanol from a mixture including ethanol and water. The subject matter can include contacting the mixture with a sorbent or membrane comprising one or more zeolites selected from the group consisting of a UFI-type zeolite, an EAB-type zeolite, and an SAT-type zeolite, wherein at least a fraction of the ethanol from the mixture is adsorbed by the sorbent or membrane and an unadsorbed portion of the mixture forms a raffinate having a lower concentration of ethanol than the mixture, and releasing adsorbed ethanol from the sorbent or membrane as a retentate or a permeant to produce an ethanol extract having a higher concentration of ethanol than the mixture.

EMBODIMENT 4 can include subject matter (such as an apparatus, a device, a method, or one or more means for performing acts), such as can include a process for separating ethanol from a mixture including ethanol and water. The subject matter can include contacting the mixture with a sorbent or membrane comprising a VFI-type zeolite, wherein at least a fraction of the ethanol from the mixture is adsorbed by the sorbent or membrane and an unadsorbed portion of the mixture forms a raffinate, the raffinate having a lower concentration of ethanol than the mixture, and releasing adsorbed ethanol from the sorbent or membrane as a retentate or a permeant to produce an ethanol extract having a higher concentration of ethanol than the mixture.

EMBODIMENT 5 can include subject matter (such as an apparatus, a device, a method, or one or more means for performing acts), such as can include a process for separating ethanol from a mixture including ethanol and water. The subject matter can include contacting the mixture with a sorbent or membrane including one of: (a) one or more zeolites selected from the group consisting of an FER-type zeolite, an MRE-type zeolite, an MTT-type zeolite, an ATN-type zeolite, a ZON-type zeolite, an OWE-type zeolite, an ESV-type zeolite, a CGF-type zeolite, an MAZ-type zeolite, a CDO-type zeolite, an STI-type zeolite, an AFO-type zeolite, an AEL-type zeolite, an ATO-type zeolite, and an EZT-type zeolite; (b) one or more zeolites selected from the group consisting of a UFI-type zeolite, an EAB-type zeolite, and an SAT-type zeolite; or (c) comprising a VFI-type zeolite; wherein at least a fraction of the ethanol from the mixture is adsorbed by the sorbent or membrane and an unadsorbed portion of the mixture forms a raffinate, the raffinate having a lower concentration of ethanol than the mixture, and releasing adsorbed ethanol from the sorbent or membrane as a retentate or a permeant to produce an ethanol extract having a higher concentration of ethanol than the mixture.

EMBODIMENT 6 can include, or can optionally be combined with, the subject matter of one or any combination of EMBODIMENTS 1-5, to optionally include any of the one or more zeolites including a channel system wherein proximate and favorable ethanol adsorption sites are spatially separated by at least 0.35 nanometers to discourage hydrogen bonds between adsorbed ethanol molecules.

EMBODIMENT 7 can include, or can optionally be combined with, the subject matter of one or any combination of EMBODIMENTS 1-6, to optionally include any of the one or more zeolites including a cage system wherein a diameter of the cage is less than 1.2 nanometers and a window connecting nearest cages is less than 0.5 nanometers.

EMBODIMENT 8 can include, or can optionally be combined with, the subject matter of one or any combination of EMBODIMENTS 1-7, to optionally include any of the one or more zeolites comprising a ratio of $SiO_2$ to $Al_2O_3$ of at least about 20:1.

EMBODIMENT 9 can include, or can optionally be combined with, the subject matter of one or any combination of EMBODIMENTS 1-8, to optionally include any of the one or more zeolites comprising a ratio of $SiO_2$ to $Al_2O_3$ of at least about 50:1.

EMBODIMENT 10 can include, or can optionally be combined with, the subject matter of one or any combination of EMBODIMENTS 1-9, to optionally include the raffinate remaining above a concentration of about 1-5 wt % ethanol.

EMBODIMENT 11 can include, or can optionally be combined with, the subject matter of one or any combination of EMBODIMENTS 1-10, to optionally include any of the one or more zeolites have an adsorption selectivity that is at least 80% of the selectivity required to yield an ethanol extract with a purity of at least 95.6 wt % ethanol.

EMBODIMENT 12 can include, or can optionally be combined with, the subject matter of one or any combination of EMBODIMENTS 1-11, to optionally include any of the one or more zeolites have an adsorption selectivity that is above the selectivity required to yield an ethanol extract with a purity of at least 95.6 wt % ethanol.

EMBODIMENT 13 can include, or can optionally be combined with, the subject matter of one or any combination of EMBODIMENTS 1-12, to optionally include any of the one or more zeolites having an ethanol adsorption capacity of at least 0.3 mol ethanol per kilogram of the zeolite sorbent or membrane when the raffinate is 1.5 wt % ethanol.

EMBODIMENT 14 can include, or can optionally be combined with, the subject matter of one or any combination of EMBODIMENTS 1-13, to optionally include any of the one or more zeolites having an ethanol adsorption capacity of at least 0.8 mol ethanol per kilogram of the zeolite sorbent or membrane when the raffinate is 5 wt % ethanol.

EMBODIMENT 15 can include, or can optionally be combined with, the subject matter of one or any combination of EMBODIMENTS 1-14, to optionally include any of the one or more zeolites comprising a channel system comprising pores with a pore size from about 1 nanometer to about 1.8 nanometers.

EMBODIMENT 16 can include, or can optionally be combined with, the subject matter of one or any combination of EMBODIMENTS 1-15, to optionally include the raffinate reaching a concentration below about 1-3 wt % ethanol at the end of the process.

EMBODIMENT 17 can include, or can optionally be combined with, the subject matter of one or any combination of EMBODIMENTS 1-16, to optionally include the any of one or more zeolites having an ethanol:water adsorption selectivity of at least 300:1 when the raffinate is 0.1 wt % ethanol.

EMBODIMENT 18 can include, or can optionally be combined with, the subject matter of one or any combination of EMBODIMENTS 1-17, to optionally include any of the one more zeolites having an ethanol adsorption capacity of at least 0.8 mol ethanol per kilogram of the zeolite sorbent or membrane when the raffinate is 0.1 wt % ethanol.

EMBODIMENT 19 can include, or can optionally be combined with, the subject matter of one or any combination of EMBODIMENTS 1-18, to optionally include any of the one more zeolites having an ethanol adsorption capacity of at least 1.5 mol ethanol per kilogram of the zeolite sorbent or membrane when the raffinate is 2 wt % ethanol.

EMBODIMENT 20 can include, or can optionally be combined with, the subject matter of one or any combination of EMBODIMENTS 1-19, to optionally include the mixture comprising one or both of a fermentation broth and a vapor above the fermentation broth.

EMBODIMENT 21 can include, or can optionally be combined with, the subject matter of one or any combination of EMBODIMENTS 1-20, to optionally include fermenting a fermentable feedstock to form the fermentation broth comprising ethanol and water.

EMBODIMENT 23 can include, or can optionally be combined with, the subject matter of one or any combination of EMBODIMENTS 1-21, to optionally include the fermentable feedstock comprising at least one of: one or more sugars; one or more starches; one or more grains; or other plant matter, such as one or more fruits, one or more vegetables, and one or more cellulosics.

EMBODIMENT 34 can include, or can optionally be combined with, the subject matter of one or any combination of EMBODIMENTS 1-22, to optionally include the fermentable feedstock comprising one or more sugars.

EMBODIMENT 35 can include, or can optionally be combined with, the subject matter of one or any combination of EMBODIMENTS 1-34 to optionally include the fermentable feedstock comprising or one or more grains or a portion thereof.

EMBODIMENT 36 can include, or can optionally be combined with, the subject matter of one or any combination of EMBODIMENTS 1-35, to optionally include the fermentable feedstock comprising one or more starches.

EMBODIMENT 37 can include, or can optionally be combined with, the subject matter of one or any combination of EMBODIMENTS 1-36, to optionally include the fermentable feedstock comprising a plant or a portion thereof.

EMBODIMENT 38 can include, or can optionally be combined with, the subject matter of one or any combination of EMBODIMENTS 1-27, to optionally include the fermentable feedstock comprising one or more fruits or a portion thereof.

EMBODIMENT 39 can include, or can optionally be combined with, the subject matter of one or any combination of EMBODIMENTS 1-38, to optionally include the fermentable feedstock comprising one or more vegetables or a portion thereof.

EMBODIMENT 40 can include, or can optionally be combined with, the subject matter of one or any combination of EMBODIMENTS 1-39, to optionally include the fermentable feedstock comprising one or more grasses or a portion thereof.

EMBODIMENT 41 can include, or can optionally be combined with, the subject matter of one or any combination of EMBODIMENTS 1-40, to optionally include the fermentable feedstock comprising one or more woods.

EMBODIMENT 42 can include, or can optionally be combined with, the subject matter of one or any combination of EMBODIMENTS 1-41, to optionally include the fermentable feedstock comprising at least one of cellulose, hemicellulose, and lignocellulose.

EMBODIMENT 43 can include subject matter (such as an apparatus, a device, a method, or one or more means for performing acts), such as can include a zeolite material for separating ethanol from a mixture including ethanol and water. The subject matter can include the zeolite material comprising one or more zeolites having a high adsorption selectivity toward ethanol over water.

EMBODIMENT 44 can include subject matter (such as an apparatus, a device, a method, or one or more means for performing acts), such as can include a zeolite material for separating ethanol from a mixture including ethanol and water. The subject matter can include the zeolite material comprising one or more zeolites selected from the group consisting of an FER-type zeolite, an MRE-type zeolite, an MU-type zeolite, an ATN-type zeolite, a ZON-type zeolite, an OWE-type zeolite, an ESV-type zeolite, a CGF-type zeolite, an MAZ-type zeolite, a CDO-type zeolite, an STI-type zeolite, an AFO-type zeolite, an AEL-type zeolite, an ATO-type zeolite, and an EZT-type zeolite, wherein the one or more zeolites have a high adsorption selectivity toward ethanol over water.

EMBODIMENT 45 can include subject matter (such as an apparatus, a device, a method, or one or more means for performing acts), such as can include a zeolite material for separating ethanol from a mixture including ethanol and water. The subject matter can include the zeolite material comprising one or more zeolites selected from the group consisting of a UFI-type zeolite, an EAB-type zeolite, and an SAT-type zeolite, wherein the one or more zeolites have a high adsorption selectivity toward ethanol over water.

EMBODIMENT 46 can include subject matter (such as an apparatus, a device, a method, or one or more means for performing acts), such as can include a zeolite material for separating ethanol from a mixture including ethanol and water. The subject matter can include the zeolite material comprising a VFI-type zeolite having a high adsorption selectivity toward ethanol over water.

EMBODIMENT 47 can include subject matter (such as an apparatus, a device, a method, or one or more means for performing acts), such as can include a zeolite material for separating ethanol from a mixture including ethanol and water. The subject matter can include the zeolite material comprising one of: (a) one or more zeolites selected from the group consisting of an FER-type zeolite, an MRE-type zeolite, an MU-type zeolite, an ATN-type zeolite, a ZON-type zeolite, an OWE-type zeolite, an ESV-type zeolite, a CGF-type zeolite, an MAZ-type zeolite, a CDO-type zeolite, an STI-type zeolite, an AFO-type zeolite, an AEL-type zeolite, an ATO-type zeolite, and an EZT-type zeolite; (b) one or more zeolites selected from the group consisting of a UFI-type zeolite, an EAB-type zeolite, and an SAT-type zeolite; or (c) a VFI-type zeolite; wherein the zeolite materials has a high adsorption selectivity toward ethanol over water.

EMBODIMENT 48 can include, or can optionally be combined with, the subject matter of one or any combination of EMBODIMENTS 43-47, to optionally include any of the one or more zeolites including a channel system wherein proximate and favorable adsorption sites are spatially separated by at least 0.35 nanometers to discourage hydrogen bonds between adsorbed molecules.

EMBODIMENT 49 can include, or can optionally be combined with, the subject matter of one or any combination of EMBODIMENTS 43-48, to optionally include any of the one or more zeolites comprising a cage system wherein a diameter of the cage is less than 1.2 nanometers and a window connecting nearest cages is less than 0.5 nanometers.

EMBODIMENT 50 can include, or can optionally be combined with, the subject matter of one or any combination of EMBODIMENTS 43-49, to optionally include any of the one or more zeolites comprising a ratio of $SiO_2$ to $Al_2O_3$ of at least about 20:1.

EMBODIMENT 51 can include, or can optionally be combined with, the subject matter of one or any combination of EMBODIMENTS 43-50, to optionally include any of the one or more zeolites comprising a ratio of $SiO_2$ to $Al_2O_3$ of at least about 50:1.

EMBODIMENT 52 can include, or can optionally be combined with, the subject matter of one or any combination of EMBODIMENTS 43-51, to optionally include any of the one or more zeolites having an adsorption selectivity that is at least 80% of the selectivity required to yield an ethanol extract with a purity of at least 95.6 wt % ethanol.

EMBODIMENT 53 can include, or can optionally be combined with, the subject matter of one or any combination of EMBODIMENTS 43-52, to optionally include any of the one or more zeolites having an adsorption selectivity that is above the selectivity required to yield an ethanol extract with a purity of at least 95.6 wt % ethanol.

EMBODIMENT 54 can include, or can optionally be combined with, the subject matter of one or any combination of EMBODIMENTS 43-53, to optionally include any of the one or more zeolites having an ethanol adsorption capacity of at least 0.3 mol ethanol per kilogram of the zeolite material when a raffinate is 1.5 wt % ethanol.

EMBODIMENT 55 can include, or can optionally be combined with, the subject matter of one or any combination of EMBODIMENTS 43-54, to optionally include any of the one or more zeolites have an ethanol adsorption capacity of at least 0.8 mol ethanol per kilogram of the zeolite material when the raffinate is 5 wt % ethanol.

EMBODIMENT 56 can include, or can optionally be combined with, the subject matter of one or any combination of EMBODIMENTS 43-55, to optionally include any of the one or more zeolites including a channel system comprising pores with a pore size from about 1 nanometer to about 1.8 nanometers.

EMBODIMENT 57 can include, or can optionally be combined with, the subject matter of one or any combination of EMBODIMENTS 43-56, to optionally include any of the one or more zeolites having an ethanol:water adsorption selectivity of at least 300:1 when a raffinate is 0.1 wt % ethanol.

EMBODIMENT 58 can include, or can optionally be combined with, the subject matter of one or any combination of EMBODIMENTS 43-57, to optionally include any of the one or more zeolites having an ethanol adsorption capacity of at least 0.8 mol ethanol per kilogram of the zeolite material when a raffinate is 0.1 wt % ethanol.

EMBODIMENT 59 can include, or can optionally be combined with, the subject matter of one or any combination of EMBODIMENTS 43-58, to optionally include any of the one or more zeolites having an ethanol adsorption capacity of at least 1.5 mol ethanol per kilogram of the zeolite material when the raffinate is 2 wt % ethanol.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a molding system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented, at least in part. Some examples can include a computer-readable medium or machine-readable medium encoded with instructions operable to configure an electronic device to perform methods or method steps as described in the above examples. An implementation of such methods or method steps can include code, such as micro-code, assembly language code, a higher-level language code, or the like. Such code can include computer readable instructions for performing various methods. The code may form portions of computer program products. The code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The Abstract is provided to allow the reader to quickly ascertain the nature of the technical disclosure. It is submitted with the understanding that it will not be used to interpret or limit the scope or meaning of the claims.

Although the invention has been described with reference to exemplary embodiments, workers skilled in the art will recognize that changes may be made in form and detail without departing from the spirit and scope of the invention.

What is claimed is:

1. A process for separating ethanol from a mixture including ethanol and water, the process comprising:
  contacting the mixture with a sorbent or membrane including one or more zeolites selected from the group consisting of:
    an MRE-type zeolite, an MTT-type zeolite, an ATN-type zeolite, a ZON-type zeolite, an OWE-type zeolite, an ESV-type zeolite, a CGF-type zeolite, an MAZ-type zeolite, an STI-type zeolite, an AFO-type zeolite, an AEL-type zeolite, an ATO-type zeolite, or an EZT-type zeolite, wherein at least a fraction of the ethanol from the mixture is adsorbed by the sorbent or membrane and an unadsorbed portion of the mixture forms a raffinate having a lower concentration of ethanol than the mixture, wherein the one or more zeolites include a channel system wherein proximate and favorable ethanol adsorption sites are spatially separated by at least 0.35 nanometers to discourage hydrogen bonds between adsorbed ethanol molecules; and releasing adsorbed ethanol from the sorbent or membrane as a retentate or a permeant to produce an ethanol extract having a higher concentration of ethanol than the mixture.

2. A process for separating ethanol from a mixture including ethanol and water, the process comprising:

contacting the mixture with a sorbent or membrane comprising one or more zeolites selected from the group consisting of an EAB-type zeolite or an SAT-type zeolite, wherein at least a fraction of the ethanol from the mixture is adsorbed by the sorbent or membrane and an unadsorbed portion of the mixture forms a raffinate having a lower concentration of ethanol than the mixture; and releasing adsorbed ethanol from the sorbent or membrane as a retentate or a permeant to produce an ethanol extract having a higher concentration of ethanol than the mixture.

3. The process of claim 1, wherein the one or more zeolites comprise a ratio of $SiO_2$ to $Al_2O_3$ of at least about 20:1.

4. The process of claim 1, wherein the one or more zeolites comprise a ratio of $SiO_2$ to $Al_2O_3$ of at least about 50:1.

5. The process of claim 1, wherein the raffinate remains above a concentration of about 1-5 wt % ethanol.

6. The process of claim 1, wherein the one or more zeolites have an adsorption selectivity that is at least 80% of the selectivity required to yield an ethanol extract with a purity of at least 95.6 wt % ethanol.

7. The process of claim 1, wherein the one or more zeolites have an ethanol adsorption capacity of at least 0.3 mol ethanol per kilogram of the zeolite sorbent or membrane when the raffinate is 1.5 wt % ethanol.

8. The process of claim 1, wherein the one or more zeolites have an ethanol adsorption capacity of at least 0.8 mol ethanol per kilogram of the zeolite sorbent or membrane when the raffinate is 5 wt % ethanol.

9. A process for separating ethanol from a mixture including ethanol and water, the process comprising:

contacting the mixture with a sorbent or membrane comprising a VFI-type zeolite, wherein at least a fraction of the ethanol from the mixture is adsorbed by the sorbent or membrane and an unadsorbed portion of the mixture forms a raffinate, the raffinate having a lower concentration of ethanol than the mixture; and releasing adsorbed ethanol from the sorbent or membrane as a retentate or a permeant to produce an ethanol extract having a higher concentration of ethanol than the mixture.

10. The process of claim 9, wherein the raffinate reaches a concentration below about 1-3 wt % ethanol at the end of the process.

11. The process of claim 9, wherein the VFI-type zeolite has an ethanol:water adsorption selectivity of at least 300:1 when the raffinate is 0.1 wt % ethanol.

12. The process of claim 9, wherein the VFI-type zeolite has an ethanol adsorption capacity of at least 0.8 mol ethanol per kilogram of the zeolite sorbent or membrane when the raffinate is 0.1 wt % ethanol.

13. The process of claim 9, wherein the VFI-type zeolite has an ethanol adsorption capacity of at least 1.5 mol ethanol per kilogram of the zeolite sorbent or membrane when the raffinate is 2 wt % ethanol.

14. The process of claim 1, further comprising fermenting a fermentable feedstock to form a fermentation broth comprising ethanol and water, wherein the mixture comprises one or both of the fermentation broth or a vapor that forms above the fermentation broth.

15. The process of claim 2, wherein the one or more zeolites comprise a ratio of $SiO_2$ to $Al_2O_3$ of at least about 20:1.

16. The process of claim 2, wherein the one or more zeolites comprise a ratio of $SiO_2$ to $Al_2O_3$ of at least about 50:1.

17. The process of claim 2, wherein the one or more zeolites have an adsorption selectivity that is at least 80% of the selectivity required to yield an ethanol extract with a purity of at least 95.6 wt % ethanol.

18. The process of claim 2, wherein the one or more zeolites have an ethanol adsorption capacity of at least 0.3 mol ethanol per kilogram of the zeolite sorbent or membrane when the raffinate is 1.5 wt % ethanol.

19. The process of claim 2, wherein the one or more zeolites have an ethanol adsorption capacity of at least 0.8 mol ethanol per kilogram of the zeolite sorbent or membrane when the raffinate is 5 wt % ethanol.

20. The process of claim 2, further comprising fermenting a fermentable feedstock to form a fermentation broth comprising ethanol and water, wherein the mixture comprises one or both of the fermentation broth or a vapor that forms above the fermentation broth.

21. The process of claim 9, further comprising fermenting a fermentable feedstock to form a fermentation broth comprising ethanol and water, wherein the mixture comprises one or both of the fermentation broth or a vapor that forms above the fermentation broth.

* * * * *